United States Patent
Gagliano

(10) Patent No.: US 11,612,694 B2
(45) Date of Patent: Mar. 28, 2023

(54) ASSISTED INJECTION DEVICE FOR INJECTING A COMPOSITION CONTAINED IN A MEDICAL CONTAINER WITH REDUCED EFFORTS

(71) Applicant: Becton Dickinson France, Le Pont de Claix (FR)

(72) Inventor: Julien Gagliano, Grenoble (FR)

(73) Assignee: Becton Dickinson France, Le Pont de Claix (FR)

( * ) Notice: Subject to any disclaimer, the term of this patent is extended or adjusted under 35 U.S.C. 154(b) by 381 days.

(21) Appl. No.: 16/632,523

(22) PCT Filed: Jul. 20, 2018

(86) PCT No.: PCT/EP2018/069701
§ 371 (c)(1),
(2) Date: Jan. 20, 2020

(87) PCT Pub. No.: WO2019/016346
PCT Pub. Date: Jan. 24, 2019

(65) Prior Publication Data
US 2020/0188597 A1    Jun. 18, 2020

(30) Foreign Application Priority Data

Jul. 21, 2017 (EP) ..................... 17305982

(51) Int. Cl.
*A61M 5/315* (2006.01)
*A61M 5/20* (2006.01)

(52) U.S. Cl.
CPC ...... *A61M 5/31505* (2013.01); *A61M 5/2033* (2013.01); *A61M 2005/2026* (2013.01);
(Continued)

(58) Field of Classification Search
CPC ............ A61M 5/2033; A61M 5/31505; A61M 2005/2026; A61M 2005/2073; A61M 2005/2086
(Continued)

(56) References Cited

U.S. PATENT DOCUMENTS 4,316,463 A * 2/1982 Schmitz .............. A61M 5/2033
                                                        604/157
4,386,606 A * 6/1983 Tretinyak ......... A61B 5/150389
                                                        604/220
(Continued)

FOREIGN PATENT DOCUMENTS

CN       102740908 A    10/2012
CN       203861697 U    10/2014
(Continued)

*Primary Examiner* — Bhisma Mehta
*Assistant Examiner* — Nidah Hussain
(74) *Attorney, Agent, or Firm* — The Webb Law Firm

(57) ABSTRACT

The present disclosure relates to an assisted injection device for injecting a composition contained in a medical container. The injection device includes a body adapted to receive a medical container in a fixed position relative to the body. The injection device includes a spring-loaded piston rod translationally movable inside the body between a proximal rest position allowing inserting of the medical container in the body and a distal operative position wherein the piston rod engages a stopper of the medical container and pushes the stopper in the medical container. The injection device includes a blocking system comprising a locking member mounted on the body and configured to engage the piston rod. The piston rod includes a proximal end extending out of the body and configured to be pushed by the user in a distal direction to accelerate the movement of the piston rod to the distal operative position.

14 Claims, 15 Drawing Sheets

(52) U.S. Cl.
CPC ............... *A61M 2005/2073* (2013.01); *A61M 2005/2086* (2013.01)

(58) Field of Classification Search
USPC ........................................................ 604/220
See application file for complete search history.

(56) References Cited

U.S. PATENT DOCUMENTS

| | | | | | |
|---|---|---|---|---|---|
| 4,698,055 | A | * | 10/1987 | Sealfon | A61M 5/284 604/82 |
| 5,226,897 | A | * | 7/1993 | Nevens | A61M 5/31511 604/218 |
| 5,269,766 | A | * | 12/1993 | Haber | A61M 5/3257 604/232 |
| 2001/0021823 | A1 | | 9/2001 | Nemoto | |
| 2015/0238700 | A1 | | 8/2015 | Jugl et al. | |
| 2015/0320935 | A1 | * | 11/2015 | Dungar | B01F 31/40 604/91 |

FOREIGN PATENT DOCUMENTS

| | | |
|---|---|---|
| DE | 202004016790 U1 | 12/2004 |
| JP | S113654 | 3/1936 |
| JP | H0767959 A | 3/1995 |
| JP | 2002224218 A | 8/2002 |
| JP | 2003513762 A | 4/2003 |
| JP | 2008307241 A | 12/2008 |
| JP | 2015525661 A | 9/2015 |
| WO | 2007002053 A2 | 1/2007 |
| WO | 2008005315 A2 | 1/2008 |
| WO | 2011032513 A1 | 3/2011 |
| WO | 2015059201 A1 | 4/2015 |

\* cited by examiner

ASSISTED INJECTION DEVICE FOR INJECTING A COMPOSITION CONTAINED IN A MEDICAL CONTAINER WITH REDUCED EFFORTS

CROSS-REFERENCE TO RELATED APPLICATIONS

This application is the United States national phase of International Application No. PCT/EP2018/069701 filed Jul. 20, 2018, and claims priority to European Patent Application No. 17305982.5 filed Jul. 21, 2017, the disclosures of which are hereby incorporated by reference in their entirety.

BACKGROUND OF THE INVENTION

Field

The disclosure relates to an assisted injection device for injecting a composition contained in a medical container. The injection device makes the injection of the composition easier for a user who needs to provide less effort for injecting the composition, especially when the composition has a high viscosity as well as controlling the injection rate while performing the injection.

Background Art

Prefilled injection devices are common containers to deliver drugs or vaccines to patients and include syringes, cartridges and autoinjectors or the like. They usually comprise a sealing stopper in gliding engagement into a container, the container being filled with a pharmaceutical composition in order to provide the practitioners with a ready-to-use injection device for patients.

A container has a substantially cylindrical shape, and comprises a proximal end able to be stoppered by a sealing stopper, a distal end wherein the pharmaceutical composition is expelled from the container, and a peripheral wall extending between the proximal end and the distal end of the container. In practice, the sealing stopper is aimed at gliding, upon the pressure exerted by a piston rod, from a proximal end of the container body towards the distal end of the container body, thereby expelling the drug contained into the container body.

When compared to empty injection devices that are filled with a vial-stored pharmaceutical composition just prior to the injection to the patient's body, the use of prefilled injection devices leads to several advantages. In particular, by limiting the preparation prior to the injection, the prefilled injection devices provide a reduction of medical dosing errors, a minimized risk of microbial contamination and an enhanced convenience of use for the practitioners. Furthermore, such prefilled containers may encourage and simplify self-administration by the patients which allows reducing the cost of therapy and increasing the patient adherence. Finally, prefilled injection devices reduce loss of valuable pharmaceutical composition that usually occurs when a pharmaceutical composition is transferred from a vial to a non-prefilled injection device. This results in a greater number of possible injections for a given manufacturing batch of pharmaceutical composition thus reducing buying and supply chain costs.

In certain cases, the injection of the composition contained in the container with a manual injection device such as a syringe can be difficult to carry out, due to the force that needs to be applied onto the piston rod for expelling the composition. It occurs for example when the composition has a high viscosity, and/or when the injection is carried out manually by a user that cannot push on the piston rod strongly enough with his fingers, for example when suffering from rheumatoid arthritis or from any type of disease affecting the user's hand or fingers. The injection may be a self-injection or may be performed by a user, such as a health care professional, to another person. In the case of healthcare professionals performing repetitive injections of viscous drugs to patients, the repetition of the same gesture requiring high force applied on the plunger rod to make the injection may cause repetitive strain injuries.

Autoinjectors can assist the user in performing an automatic injection of the pharmaceutical composition. They usually comprise an injection button the user needs to press in order to start the injection.

However, the user cannot change the injection rate (or injection speed) while performing the injection with an autoinjector. In other terms, it is not possible to increase or decrease the injection rate while performing the injection.

This lack of control of the injection rate can generate pain and anxiety to the user, and may lead the user to be unable to perform the injection correctly.

Moreover, similarly to manual injection devices, autoinjectors can encounter difficulties for injecting a composition with a high viscosity, mainly due to an insufficient force applied to the piston by the injection mechanism. Hence, the composition is not expelled from the container, or at most expelled at a very low speed.

SUMMARY

In view of the foregoing, there is a strong need for an injection device for injecting a pharmaceutical composition contained in a medical container which allows for an easier injection of the composition compared to the existing injection devices, in particular when the composition has a high viscosity and/or when the user has a reduced physical strength. There is also a need for such an injection device that allows the user to control the injection, in particular to adjust the injection rate while performing the injection.

An object of the disclosure is thus to provide an assisted injection device for injecting a pharmaceutical composition contained in a medical container that overcomes the drawbacks of the known devices.

One object of the disclosure is an assisted injection device for injecting a composition contained in a medical container, comprising:
  a body adapted to receive a medical container in a fixed position relative to the body, the body being configured to be held in a user's hand,
  a spring-loaded piston rod translationally movable inside the body between a proximal rest position and a distal operative position wherein the piston rod engages a stopper of the medical container and pushes the stopper in the medical container,
  a blocking system comprising a locking member configured to engage the piston rod, the locking member being movable between a locked position wherein the locking member retains the piston rod in the proximal rest position, and a released position wherein the locking member allows the piston rod to move from the proximal rest position to the distal operative position under the force of the spring,
  wherein the piston rod includes a proximal end extending out of the body and configured to be pushed by the user in a distal direction to accelerate the movement of the piston rod to the distal operative position when the locking member is in the released position.

In this application, the "distal direction" is to be understood as meaning the direction of injection, with respect to the medical container the device of the disclosure is to be mounted on. The distal direction corresponds to the travel direction of the piston rod during the injection, the medical composition contained initially in the medical container being expelled from the latter. The "proximal direction" is to be understood as meaning the opposite direction to said direction of injection.

According to other optional features of the device of the disclosure:
- the proximal rest position of the piston rod allows inserting of the medical container in the body;
- the locking member is mounted on the body, and in the locked position the locking member cooperates with the body to retain the piston rod in the proximal rest position, and in the released position the locking member cooperates with the body to allow the piston rod to move from the proximal rest position to the distal operative position under the force of the spring;
- the piston rod is provided with a transversal hole, and the locking member is an insert which, when in the locked position, is inserted radially in the transversal hole of the piston rod, and when in the released position, is removed from the transversal hole;
- the insert is slidable on the proximal wall of the body opposite the medical container;
- the proximal wall of the body comprises a notch adapted to receive the insert slidable therein, the notch extending radially to the piston rod and being aligned with the hole of the piston rod when the piston rod is in the proximal rest position;
- the peripheral wall of the body of the device is provided with a transversal opening that forms a transversal passage through said body, and when in the locked position, the insert is inserted radially in the transversal opening of the body and crosses the hole of the piston rod aligned therewith, and when in the released position, the insert is removed from the transversal opening;
- the peripheral wall of the body of the device is provided with a transversal opening that forms a transversal passage through said body, and when in the locked position, the insert is inserted radially in the transversal opening of the body distally from the piston rod, so that the piston rod abuts the insert, and when in the released position, the insert is removed from the transversal through hole;
- the piston rod is provided with a narrowed section, and the locking member is a latch provided with at least a first hole and a second hole in communication with each other, the diameter of the first hole being smaller than the diameter of the piston rod and the diameter of the second hole being greater than the diameter of the piston rod, the latch being radially slidable between the locked position wherein the first hole is aligned with the piston rod and accommodates the narrowed section of the piston rod, and the released position wherein the second hole is aligned with the piston rod and crossed by said piston rod;
- the latch is slidable on the proximal wall of the body opposite the medical container (40);
- the piston rod is provided with a toothed rack, and the blocking system comprises a button mounted on the body of the device and coupled to the locking member which is a wing, the wing being pivotably mounted on a structure fixed to the body, the wing being pivotably movable between the locked position wherein the button is released and the wing engages the toothed rack so as to block the piston rod, and the released position wherein the button is pushed and the wing disengages the toothed rack so as to allow the piston rod to move;
- the button is advantageously a spring-loaded button;
- the body comprises a container holder system configured to receive at least a portion of the medical container and to hold the medical container aligned with the movement direction of the piston rod so that when moving from the proximal rest position to the distal operative position, the piston rod engages the stopper of the medical container and pushes the stopper in the medical container to inject the composition;
- the container holder system comprises:
    - a slot provided in the peripheral wall of the body that leads to a housing configured to receive at least a portion of the medical container and to maintain the medical container in a fixed position aligned with the movement direction of the piston rod,
    - a through groove provided in the distal wall of the body, continuous with the slot and extending in the distal wall from the slot, the groove being configured to guide the medical container inserted via the slot to the housing.

Another object of the disclosure is an assisted injection device assembly, comprising an assisted injection device as described previously and a medical container mounted thereon.

The assisted injection device assembly comprises optionally comprises a spacer configured to be fixed to the stopper, the spacer being configured to be contacted and pushed by the piston rod along with the stopper when the piston rod is moving from the proximal rest position to the distal operative position.

BRIEF DESCRIPTION OF THE DRAWINGS

Further features and advantages of the disclosure will become apparent from the detailed description to follow, with reference to the appended drawings, in which.

DETAILED DESCRIPTION

The disclosure proposes an assisted injection device for injecting a composition contained in a medical container.

Prior to the injection, the medical container 40 is filled with the composition intended to be injected, and stoppered with a stopper 44 inserted therein. The stoppered medical container 40 is then mounted on the device to constitute an injection device assembly, and the injection of the composition can be carried out.

Figure 1:
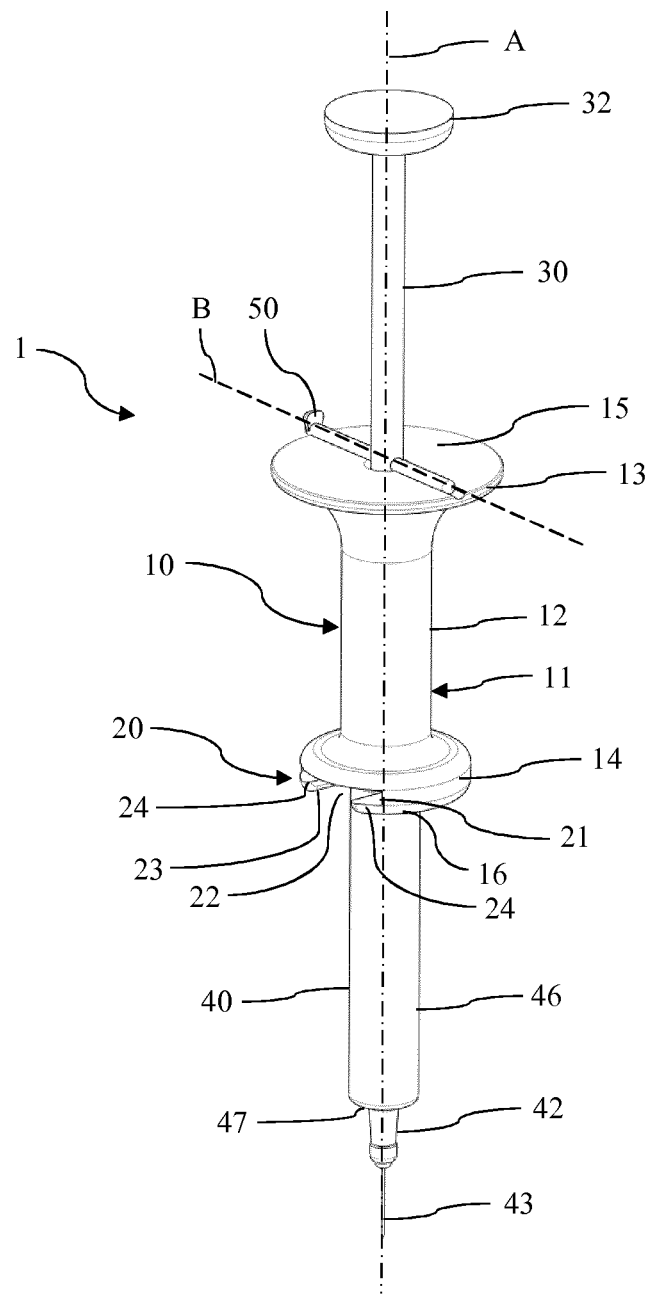
FIG. 1 is a general view in perspective of an embodiment of the injection device of the disclosure according to first embodiment of the blocking system.
Figure 2:
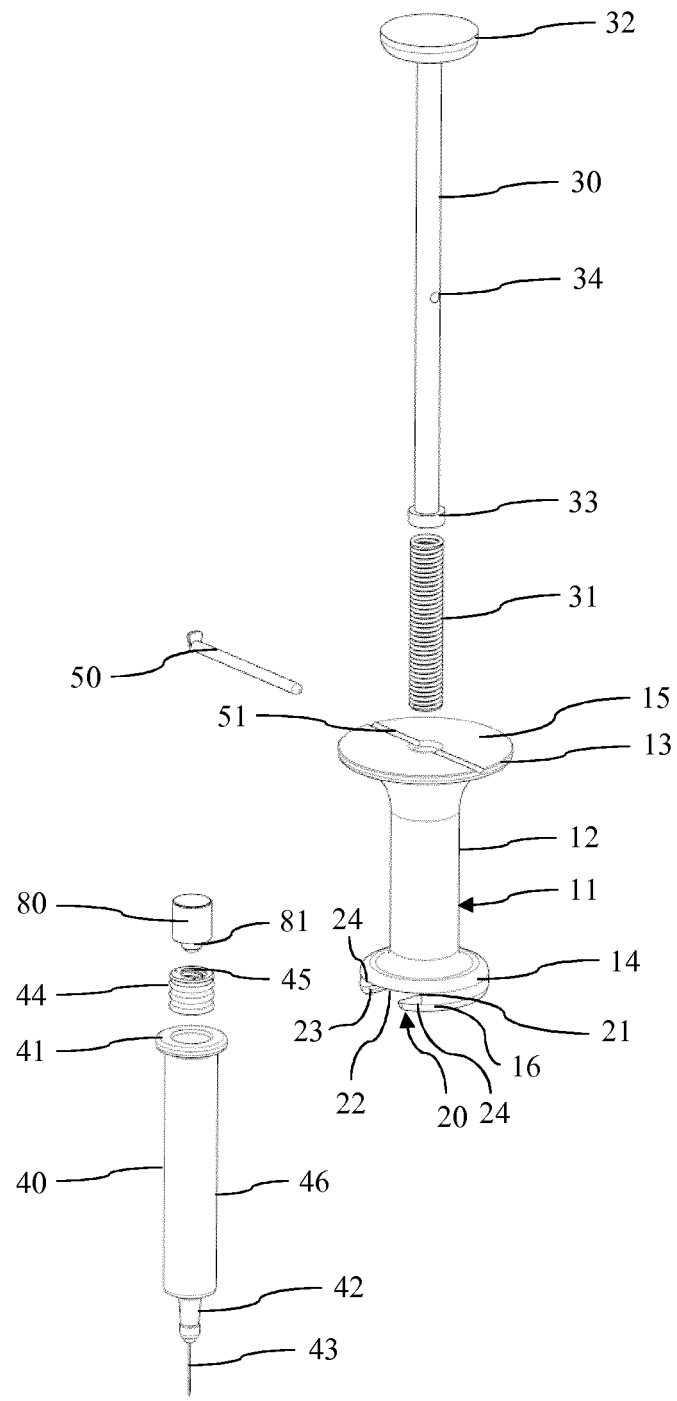
FIG. 2 is an exploded perspective view of the injection device illustrated in FIG. 1.

In reference to FIGS. 1 and 2, the injection device 1 comprises a body 10 extending along a longitudinal axis (A). The body 10 comprises a peripheral wall 11 that includes a grip surface 12 limited proximally and distally by respectively a first flange 13 and a second flange 14 that extend radially outwardly from the longitudinal axis (A). Hence, when moving or using the device, the user can easily grab the body between the flanges 13, 14. The palm of his hand contacts the grip surface 12 and the upper and lower ends of his hand abut the flanges 13, 14, thus securing the implementation of the device. Or the user can hold the grip surface 12 between his index finger and his middle finger, both abutting the flange 13, like he would normally hold a standard syringe. The device is thus handheld and the dimensions and the weight of the device are advantageously adapted for this purpose.

The medical container 40 comprises a body 46 including a proximal end 41, and a distal end having a tip 42 and a needle 43 extending from thereon. The needle 43 may be covered by a cap (not represented) to prevent any injury when handled before use.

The body 10 comprises a container holder system 20.

According to an embodiment illustrated in FIG. 1, the container holder system 20 includes a slot 21 provided in the peripheral wall 11 of the body, advantageously in the second flange 14, that leads to a housing 22 adapted to receive the proximal end 41 of the medical container 40.

The container holder system 20 further includes a through groove 23 provided in the distal wall 16 of the body, continuous with the slot 21 and extending in the distal wall from the slot. In a practical way, the proximal end of the medical container 40 is inserted through the slot 21 and moved in a radial direction along the groove 23 until the container 40 is in a fixed position in the housing 22 relative to the body 10. The groove separates two projecting parts 24 against which the proximal end 41 of the medical container 40 abuts, thereby preventing the medical container 40 from falling off the device.

To this end, the inner surface of the groove 23 contacts the body of the container 40. In particular, the groove 23 can be configured to prevent the container 40 inserted herein from moving radially, unless the container is moved by a user. The groove is preferably made of a rigid and smooth material, such as rigid plastic or metal (aluminum, stainless steel) for example, for making the insertion of the container therein easier, as well as contributing to maintain the container in a fixed position in the housing 22 during the injection.

The structure of both the slot 21 and the groove 23 may be adapted according to the type of container 40 intended to be stoppered by the device 1.

This embodiment is particularly useful when the medical container 40 is a syringe or the like, as the proximal end 41 of the container 40 is a flange that abuts the projecting parts 24.

Figure 12:
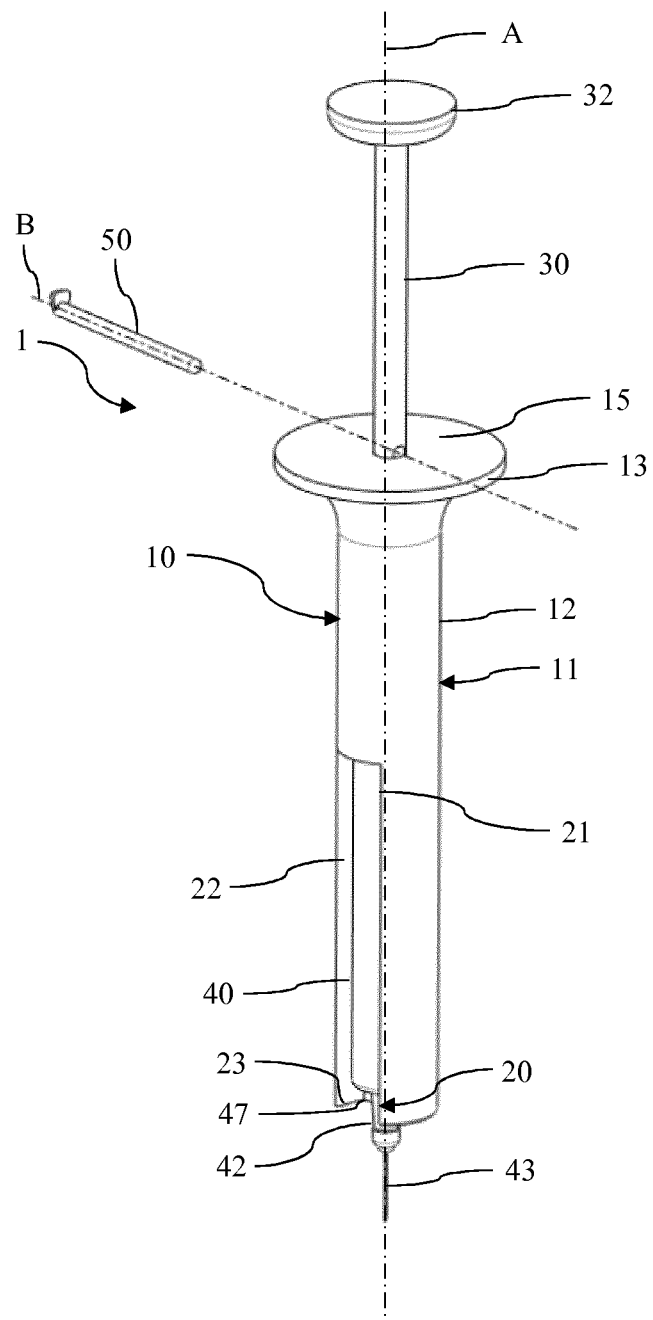
FIG. 12 is a perspective view of the device according to an embodiment of the container holder system.
Figure 13:
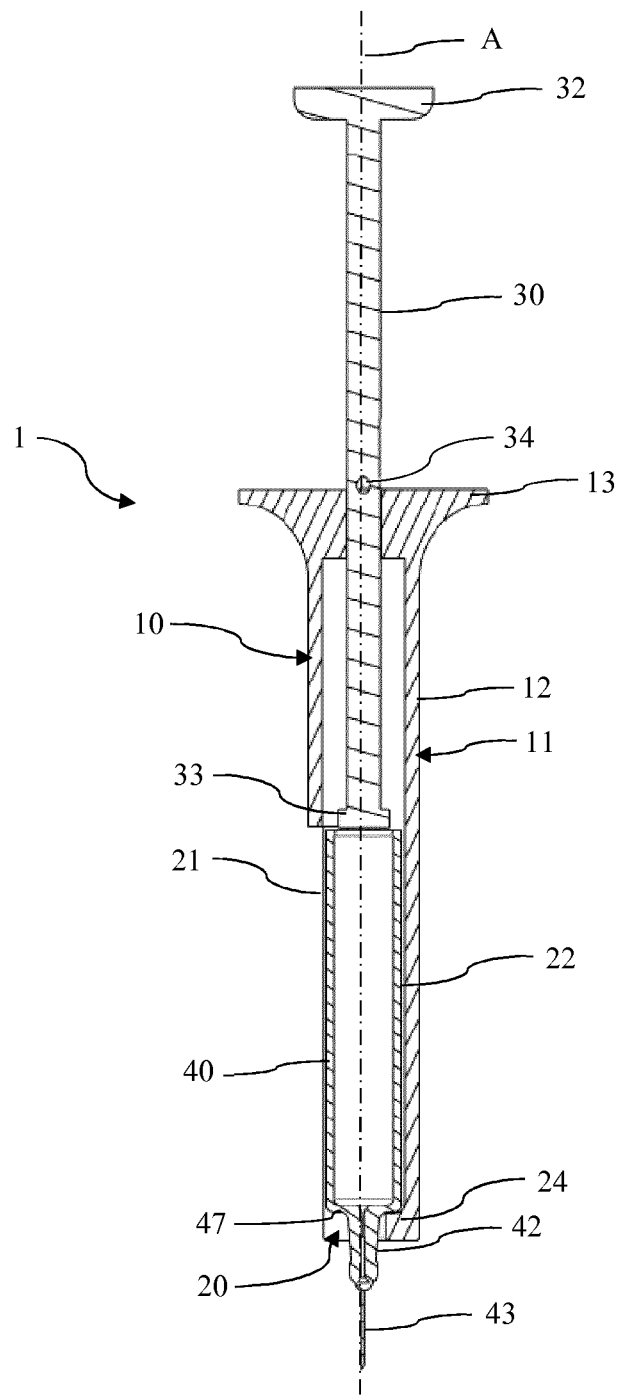
FIG. 13 is a side sectional view of the device illustrated in FIG. 12.

Alternatively, when the container 40 is a cylinder or the like (with no proximal flange), the configuration of the container holder system 20 may be adapted accordingly. According to the embodiment illustrated in FIGS. 12 and 13, the dimensions of the slot 21 and the housing 22 are adapted to receive the entire body 46 of the medical container 40 inserted therein, while the tip 42 of the container 40 is moved in a radial direction along the groove 23 until being positioned in the housing 22 where the medical container 40 is maintained in a fixed position relative to the body 10. When the container 40 is positioned in the housing 22, the shoulder 47 (between the body 46 and the tip 42) abuts the projecting parts 24 thereby avoiding the medical container 40 to fall off the device 1. Advantageously, in this situation, only the tip 42 and a needle 43 of the medical container 40 project distally out of the body 10 of the device. Of course, this embodiment may also be appropriate when the medical container 40 is a syringe or the like, the housing 22 being adapted accordingly to accommodate the flange of the medical container.

Of course, other embodiments of the container holder system are possible without departing from the scope of the disclosure. For example, the medical container 40 could be inserted longitudinally through an opening provided in the distal wall of the body 10, and secured with an insert inserted radially in a slot provided in the peripheral wall 11 of the body 10.

The device 1 comprises a piston rod 30 that extends in an internal volume 17 of the body 10 along the axis A. A spring 31 is arranged in the internal volume 17, coaxially and in contact with the piston rod 30. In that way, the spring-loaded piston rod 30 is translationally movable inside the body 10 under the force of the spring 31 along the axis (A), between a proximal rest position, and a distal operating position wherein the piston rod 30 engages the stopper 44 of the medical container 40 and pushes said stopper in the medical container.

In reference to FIGS. 2 and 3, the piston rod 30 comprises advantageously a radially enlarged proximal end 32 that serves as a pushing surface allowing the user to push the piston rod 30 in the distal direction with his thumb and as a handle allowing the user to pull the piston rod 30 back in the proximal direction by grabbing the radially enlarged proximal end 32 for example in order to carry out another injection with another container.

The injection device 1 further comprises a blocking system for retaining the piston rod 30 in the proximal rest position. The blocking system comprises a locking member 50 configured to engage the piston rod. The locking member is movable between a locked position wherein the locking member retains the piston rod 30 in the proximal rest position, and a released position wherein the locking member allows the piston rod 30 to move from the proximal rest position to the distal operative position under the force of the spring 31 in order to carry out the injection of the composition contained in the medical container 40. The blocking system will be described according to several embodiments in the following of the present text.

According to a first embodiment, the locking member is an insert 50 adapted to be removably inserted in a transversal hole 34 provided in the piston rod 30. The transversal hole 34 extends perpendicularly to the axis (A) and is preferably a through hole that extends across the piston rod. The insert 50 is represented in a non-limitative embodiment as a pin in FIGS. 1 to 5, but may be of another form provided that the insert can fulfill its function as described.

According to a first alternative of the first embodiment illustrated in FIGS. 1 to 4, the insert 50 is adapted to be slid on the proximal wall 15 of the body 10, opposite the medical container 40. Preferably, the insert 34 is adapted to be slid towards or away from the piston rod 30 in a notch 51 arranged on the proximal wall 15 of the body 10 that extends radially to the piston rod 30. In other words, the longitudinal axis (B) of the notch 51 is perpendicular to the axis (A) of the piston rod 30. When the hole 34 of the piston rod is a through hole, the notch 51 preferably extends through the proximal wall 15 of the body 10 from one point to another of the periphery of the proximal wall, on both sides of the piston rod 30. The notch may alternatively extend through a portion only of the proximal wall 15 of the body 10, on one side only of the piston rod 30.

Figure 3A:
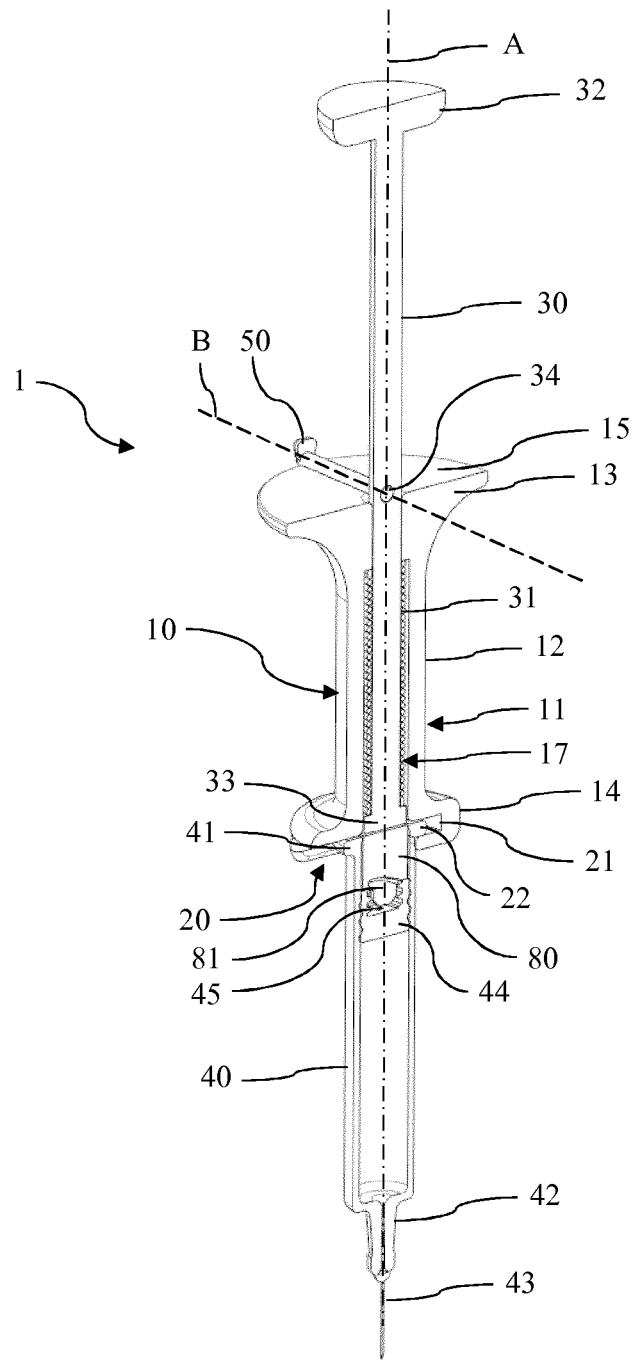
FIG. 3A is a side sectional view of the device, wherein the blocking system blocks the piston rod in a proximal rest position.

As illustrated in FIG. 3A, when the piston rod 30 is in the proximal rest position, the transversal hole 34 of the piston rod 30 is substantially radially aligned with the proximal wall 15 of the body, and the notch 51 is radially aligned with the transversal hole 34, thus allowing the insert 50 to be inserted therein. In this position, the spring 31 is compressed, and the distal end of the piston rod 30 is away from the stopper 44.

Figure 3B:
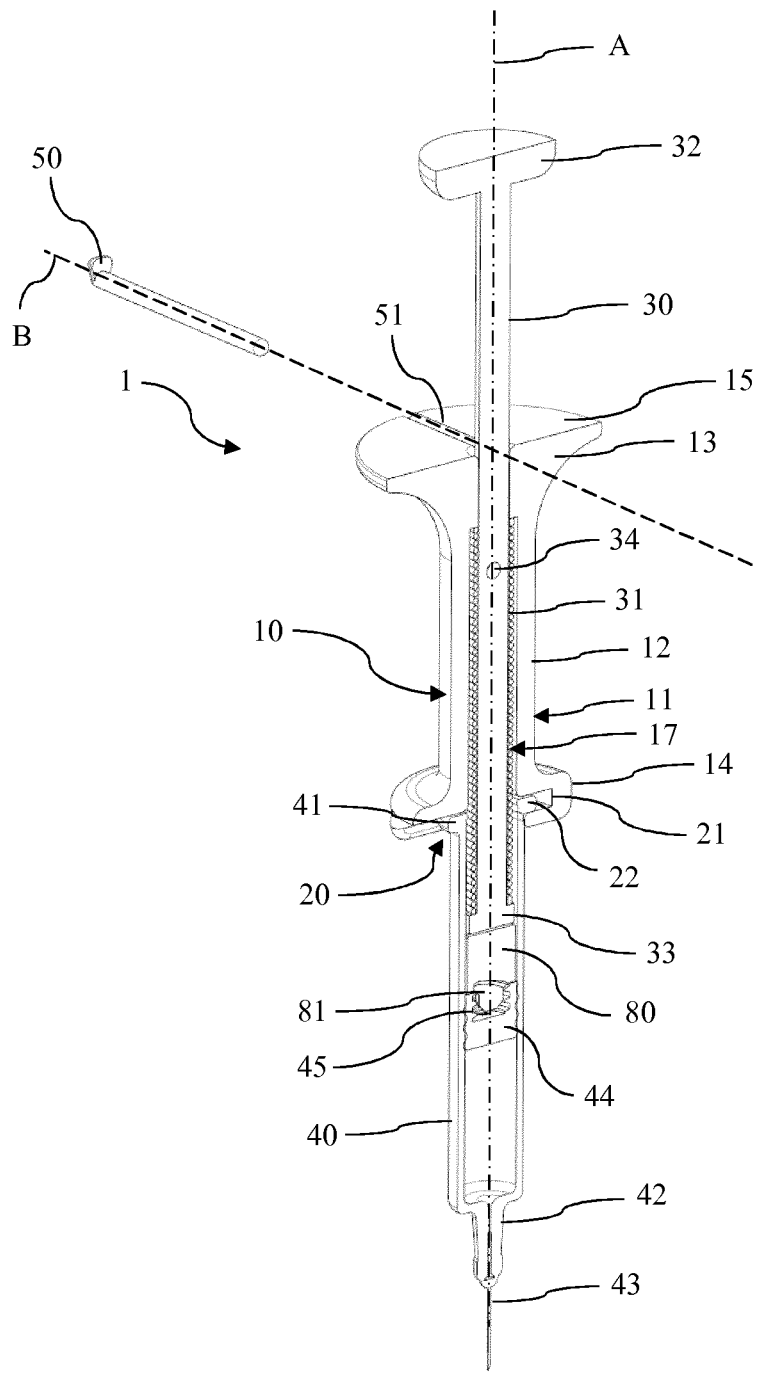
FIG. 3B is a side sectional view of the device, wherein the blocking system is released and the piston rod moved in an operative position.

In order to perform the injection, the insert 50 is removed from the transversal hole 34 of the piston rod 30 and slid back away from the piston rod, as illustrated in FIG. 3B. As a result, the spring 31 causes the piston rod 30 to move translationally in a distal direction, from the proximal rest position to the operative position wherein the piston rod 30 engages the stopper 44, and the composition is expelled from the syringe 40 via the needle 43. This movement of the piston rod 30 is due to the spring force of the spring 31 that causes the spring to return to a relaxed state wherein said spring is released. Hence, the piston rod 30 can move without any input of the user, which makes the injection easier.

Figure 4:
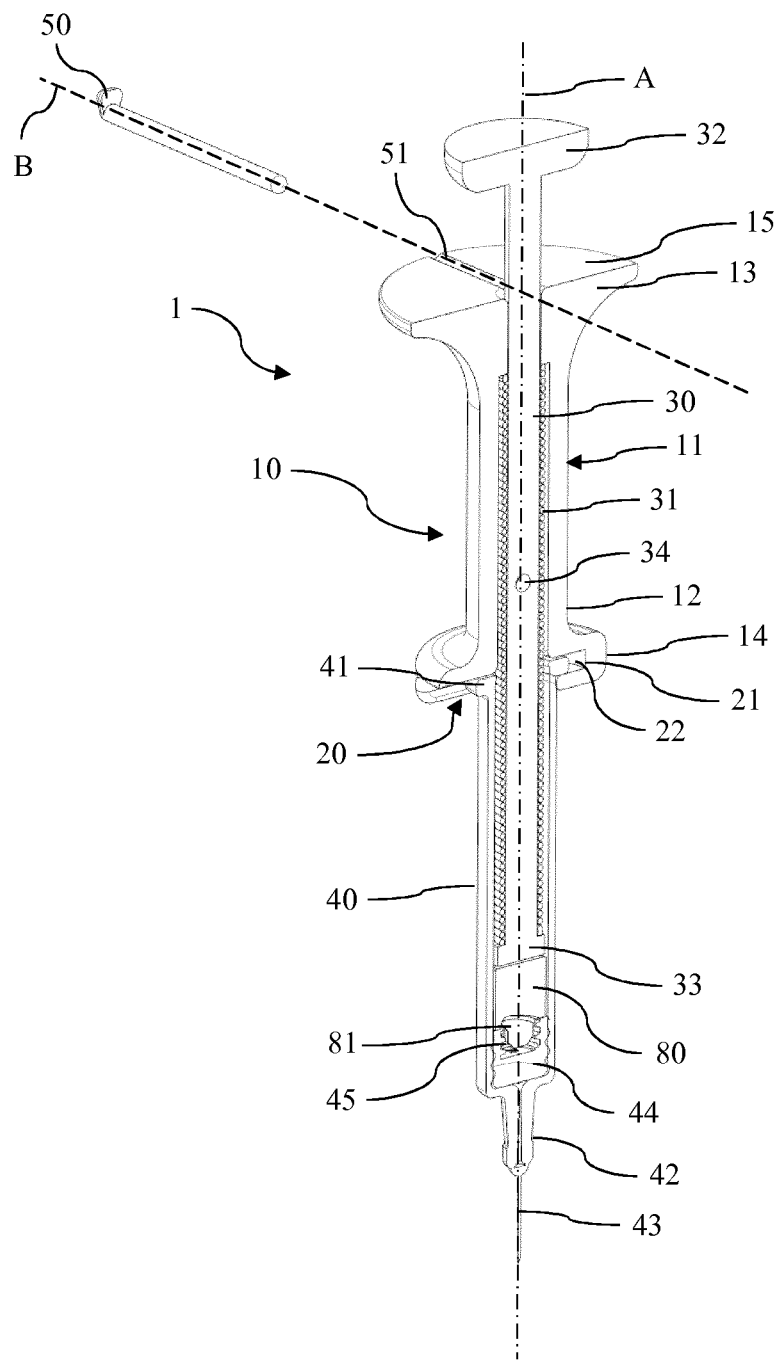
FIG. 4 is a side sectional view of the device at the end of the injection.

At the end of the injection, illustrated in FIG. 4, the entirety of the composition has been injected. The stopper 44 abuts the distal end 42 of the medical container 40, and the piston rod 30 cannot move further distally. The spring 31 is in an at least partially relaxed state, and a proximal portion of the piston rod 30 in the vicinity of its proximal end 32 remains outside the body 10 in order to allow the user to pull the piston rod 30 back to the proximal rest position for a subsequent injection to be carried out. The piston rod 30 is then blocked by the insert 50, and the empty medical container 40 is removed from the container holder system and may be replaced by another prefilled medical container to carry out another injection.

In the following, the features of the device other than the blocking system will not be described again since these features and their functioning are similar to what has been described above, taking into account the structural differences of the device according to the different embodiments.

Figure 5:
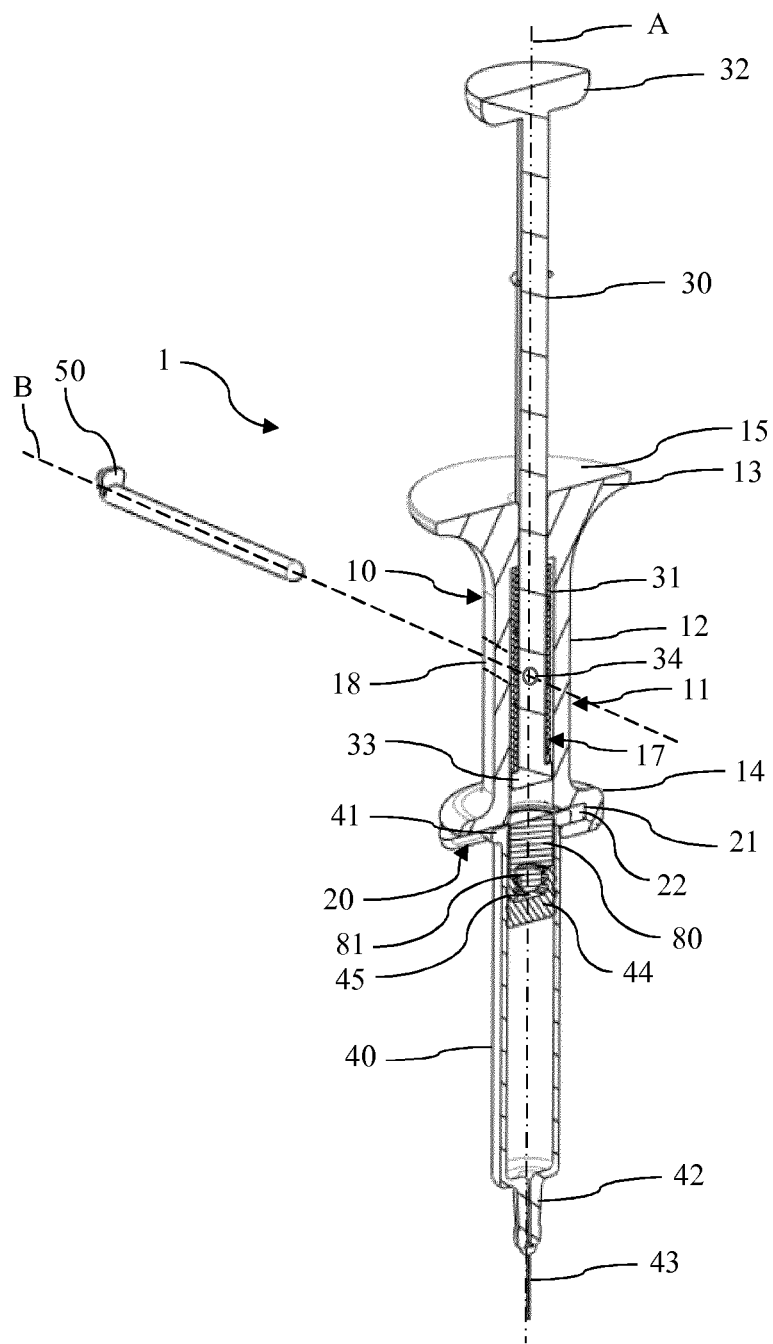
FIG. 5 is a perspective sectional view of the device according to an alternative of the first embodiment of the blocking system.

According to a second alternative of the first embodiment illustrated in FIG. 5, the insert 50 is adapted to be slid towards or away from the piston rod 30 in a transversal opening 18 provided in the peripheral wall 11 of the body 10 that forms a passage extending radially to the piston rod 30, preferably from one side of the peripheral wall 11 to the other. In other words, the longitudinal axis (B) of the transversal opening is perpendicular to the axis (A) of the piston rod 30.

When the piston rod 30 is in the proximal rest position, the transversal opening 18 is aligned with the hole 34 of the piston rod 30. The insert 50 is inserted radially in the transversal opening 18 of the body 10 and the hole 34 of the piston rod 30, thereby maintaining the piston rod in the proximal rest position. The transversal opening 18 may be positioned at different locations of the peripheral wall 11. For example, the transversal opening may be positioned between the first flange 13 and the inner volume 17 of the body 10. Otherwise the transversal opening may be positioned radially aligned with the internal volume 17 of the body 10 so as to lead to said internal volume. In this latter case, the coils of the spring are advantageously adapted so that the insert 50 can pass through the piston rod 30 via the transversal hole 34. For example, the distance between adjacent coils of the spring is greater than the diameter of the insert 50.

In order to perform the injection, the insert 50 is removed from the hole 34 of the piston rod, and from the transversal opening 18, to allow the piston rod 30 to move to the distal operative position.

Figure 6:
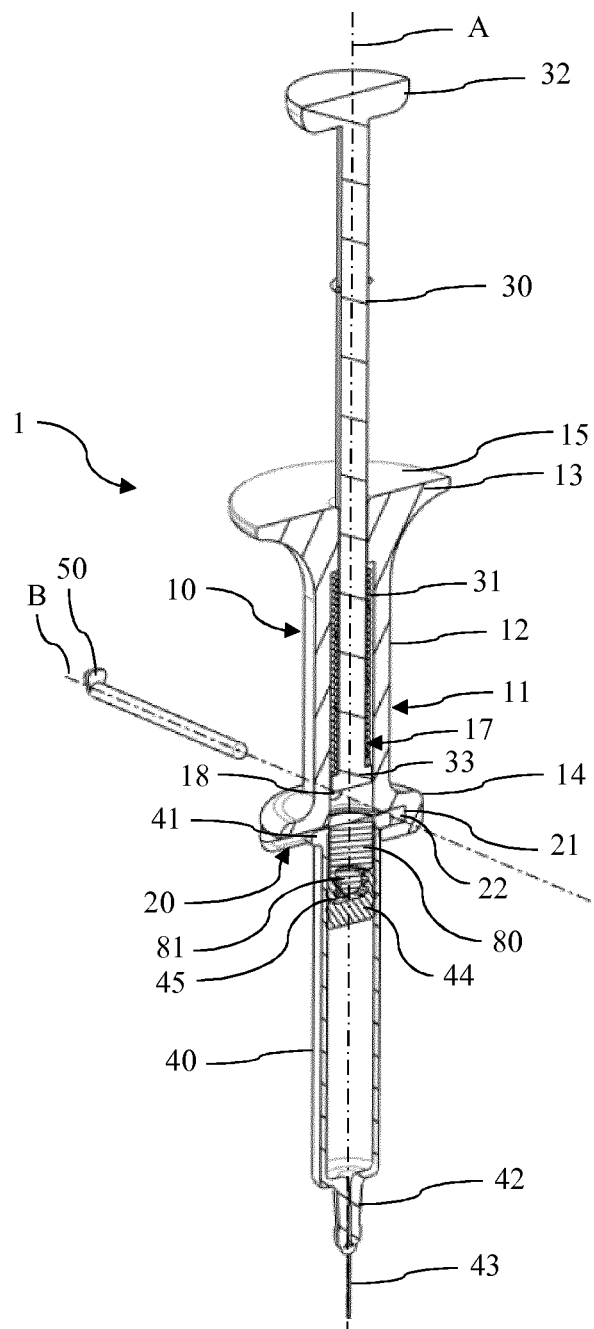
FIG. 6 is a perspective sectional view of the device according to a second embodiment of the blocking system.

According to a second embodiment illustrated in FIG. 6, the piston rod 30 does not comprise a transversal hole as described above. The locking member is an insert 50 as described in the first embodiment. The insert 50 is adapted to be slid in a transversal opening 18 provided in the peripheral wall 11 of the body 10. The transversal opening 18 has a similar structure as in the first embodiment. Said transversal opening 18 is radially aligned with the internal volume 17 of the body 10 so as to lead to said internal volume, and positioned distally from the piston rod 30 when said piston rod is in the proximal rest position. In particular, the transversal opening 18 may be provided between the second flange 14 of the body 10 and the piston rod 30 when said piston rod 30 is in the proximal rest position. When the insert 50 is inserted in the transversal opening of the body 10, the piston rod 30 being in the proximal rest position, said insert 50 extends across the inner volume of the body 10, and the distal end 33 of the piston rod 30 abuts the insert 50, thereby maintaining the piston rod in the proximal rest position.

In order to perform the injection, the insert 50 is removed from the transversal opening 18. Hence, the distal end 33 of the piston rod 30 no longer abuts the insert 50, and the piston rod moves to the distal operative position.

Figure 7:
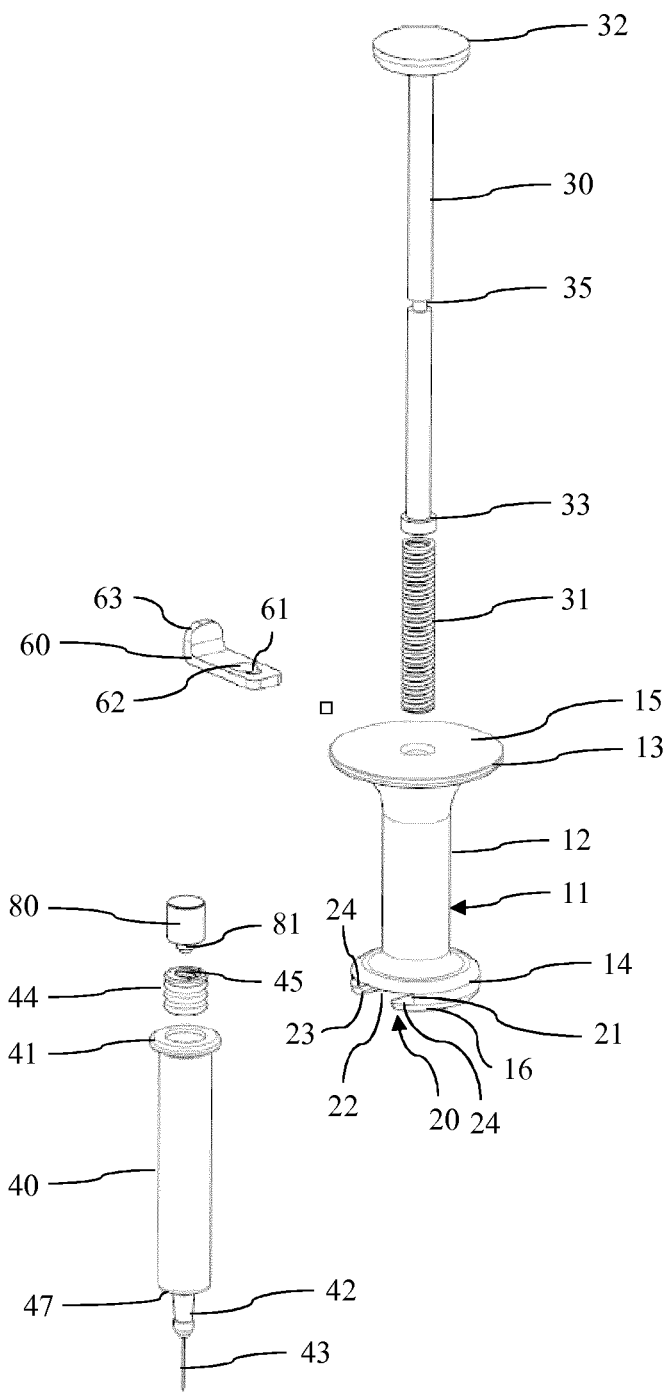
FIG. 7 is an exploded perspective view of the device according to a third embodiment of the blocking system.
Figure 8:
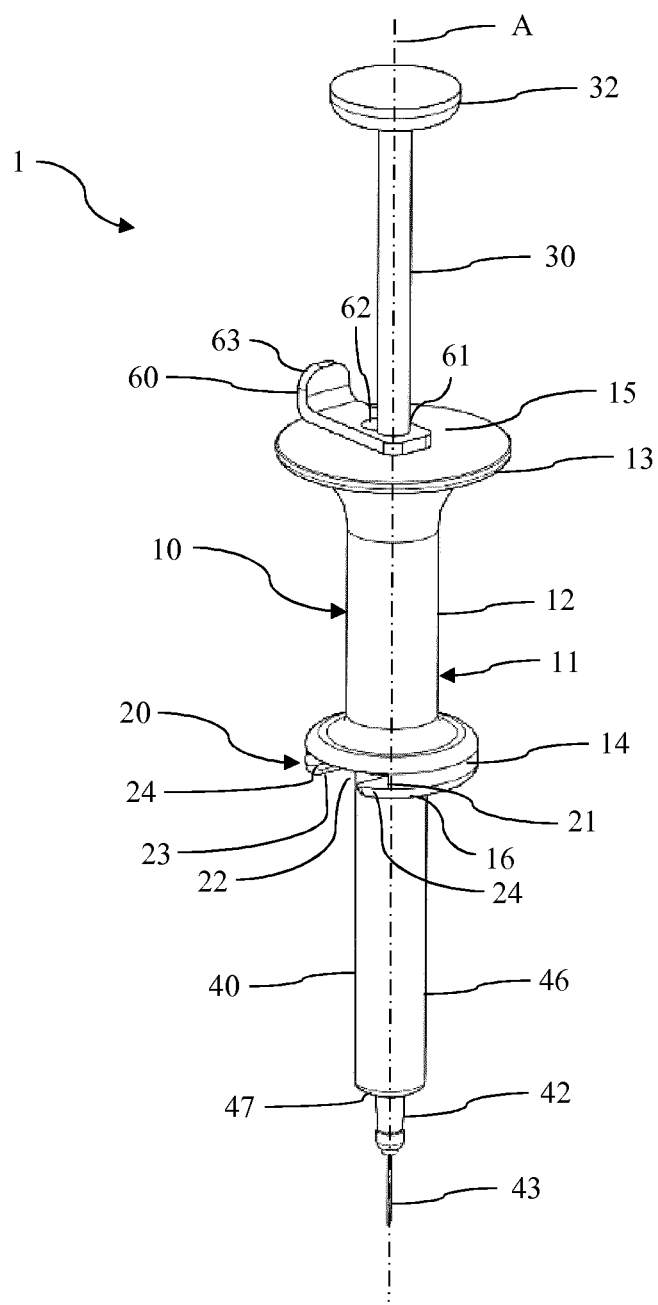
FIG. 8 is a perspective view of the device illustrated in FIG. 7, wherein the blocking system blocks the piston rod in a proximal rest position.

According to a third embodiment illustrated in FIGS. 7 and 8, the piston rod 30 is provided with a narrowed section 35 having a reduced diameter compared to that of the piston rod 30. The locking member is a latch 60 provided with a first hole 61 and a second hole 62 in communication with each other. The diameter of the first hole 61 is smaller than the diameter of the piston rod 30, and is configured to accommodate only the narrowed section 35 of the piston rod. The diameter of the second hole 62 is greater than the diameter of the piston rod 30, and is configured to accommodate the piston rod.

The latch 60 is radially slidable relatively to the body 10 and the piston rod 30, preferably on the proximal wall 15 of the body 10, by pushing or pulling the actuation zone 63.

Figure 9A:
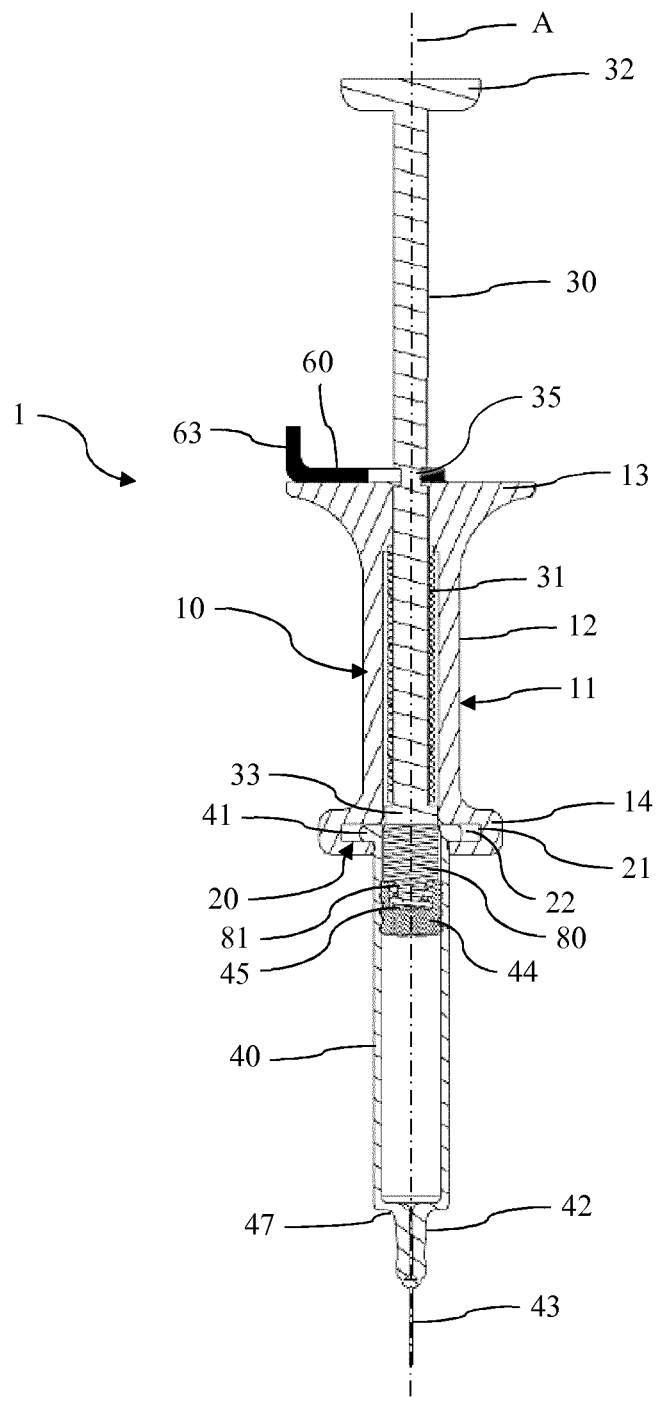
FIG. 9A is a sectional view of the device illustrated in FIG. 7, wherein the blocking system blocks the piston rod in a proximal rest position.

As illustrated in FIG. 9A when the piston rod 30 is in the proximal rest position, the first hole 61 is aligned with the piston rod 30 and accommodates the narrowed section 35 of the piston rod. The piston rod abuts the latch 60 and is thereby maintained in the proximal rest position.

Figure 9B:
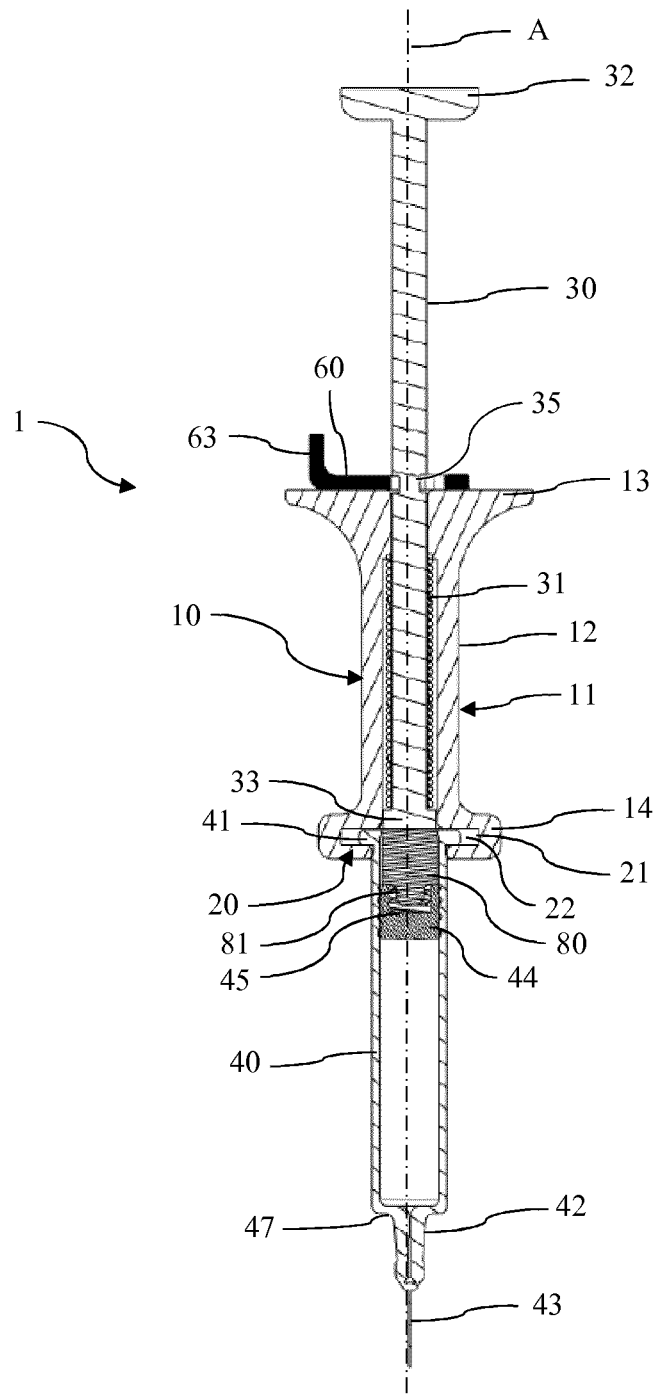
FIG. 9B is a sectional view of the device illustrated in FIG. 7, wherein the blocking system is released and the piston rod is moved in an operative position.

In order to perform the injection, the latch 60 is slid radially and inwardly by pushing the actuation zone 63, as illustrated in FIG. 9B, causing the second hole 62 to align with the piston rod 30. The piston rod 30 passes through the second hole 62 and is thus allowed to move from the proximal rest position to the operative position.

An advantage of this embodiment is that the latch remains attached to the device throughout its use, and thus cannot be lost once the piston rod is released.

Figure 10:
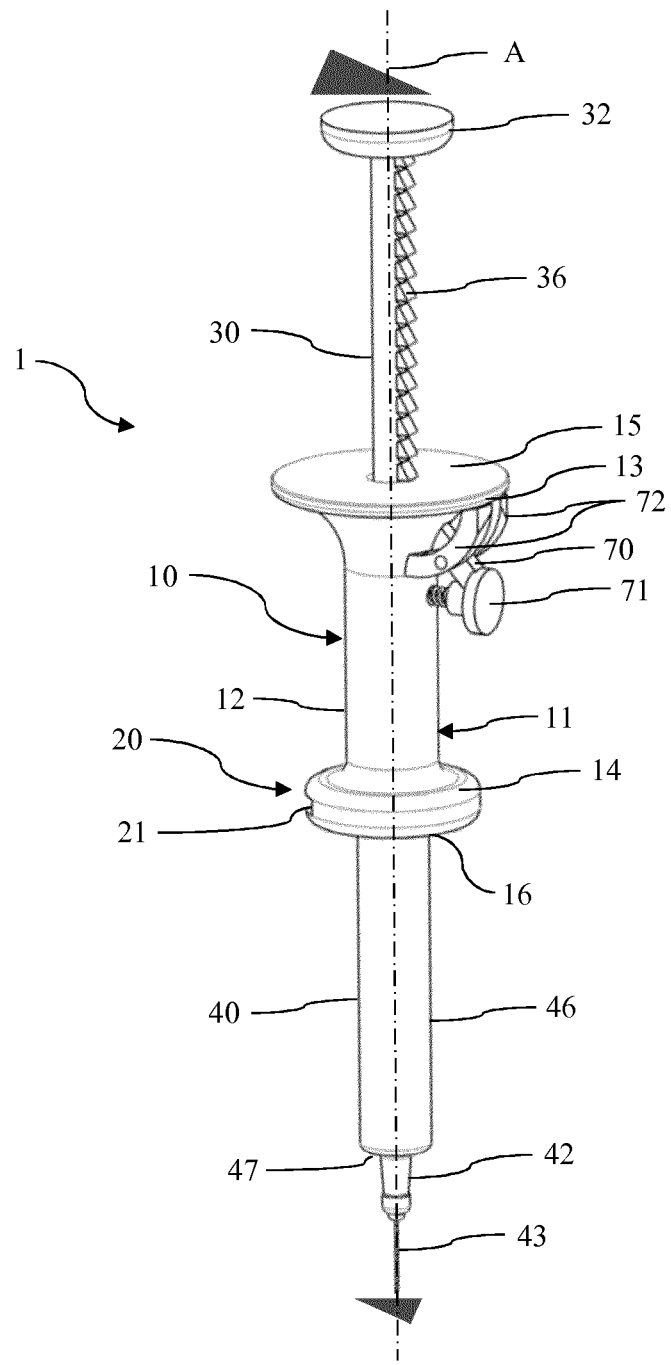
FIG. 10 is a perspective view of the device according to a fourth embodiment of the blocking system, wherein the blocking system blocks the piston rod in a proximal rest position.
Figure 11:
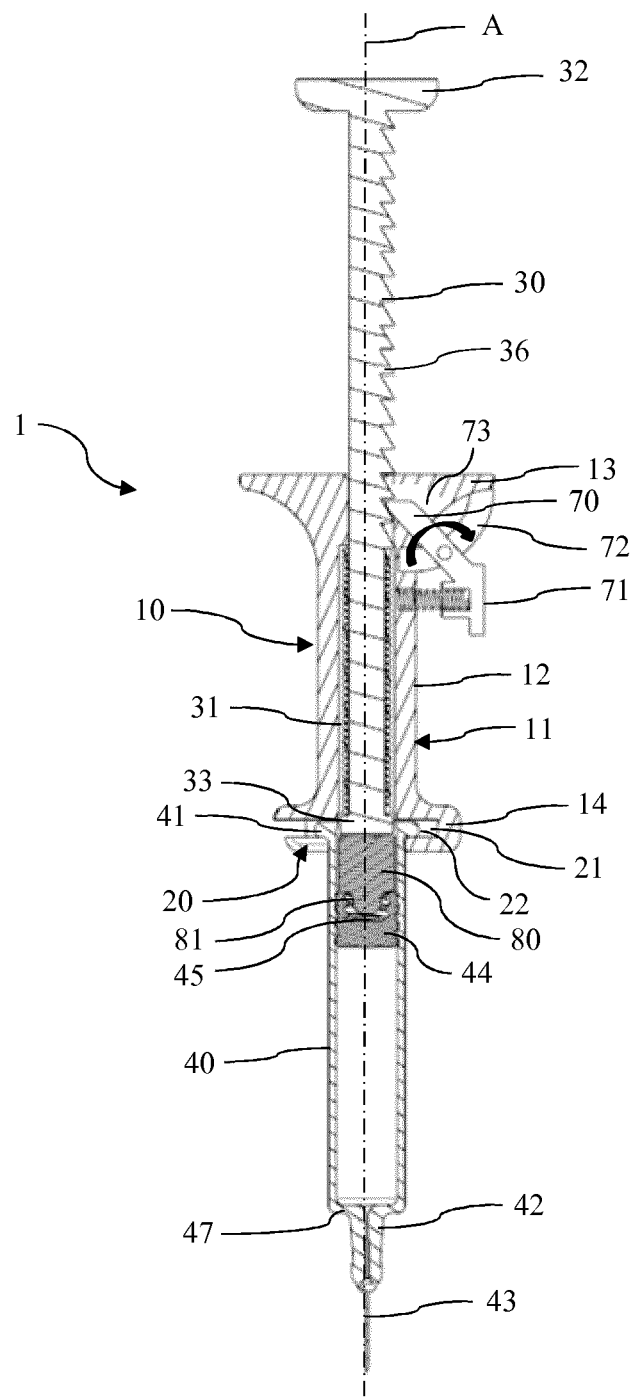
FIG. 11 is a side sectional view of the device illustrated in FIG. 10.

According to a fourth embodiment illustrated in FIGS. 10 and 11, the piston rod 30 is provided with a toothed rack 36. The blocking system comprises a button 71, preferably a spring-loaded button, mounted on the body 10 of the device 1 and coupled to the locking member which is a wing 70. The wing 70 is pivotably mounted on a structure fixed to the body 10, in a form of two branches 72, advantageously curved, joining the first flange 13 and the peripheral wall 11 of the body 10. The body 10 of the device is provided with a housing 73 configured to accommodate the wing.

As illustrated in FIG. 10, the button is released and the wing engages the toothed rack. The piston rod 30 is in the proximal rest position.

In order to perform the injection, the button 71 is pushed radially and inwardly (represented by the arrow), causing the wing 70 to pivot about the curved branches 72 away from the piston rod 30 and disengage the toothed rack 36, thereby allowing the piston rod to move from the proximal rest position to the operative position.

Regardless the embodiment of the blocking system, at the end of the injection, the device may be reset manually by the user, so as to proceed to another injection. To do so, the piston rod 30 is pulled by the user in a proximal direction back to the proximal rest position, preferably by grabbing the radially enlarged proximal end 32, and the locking member is moved in the locked position. Then, the empty medical container 40 is removed from the container holder system 20, and a new filled medical container 40 may be positioned in the container holder system 20.

The spring 31 is advantageously selected depending on the viscosity of the composition to be injected, and more generally, depending on the difficulty of performing the injection. For example, for a composition of a high viscosity, a spring with a high spring force should be preferentially selected.

While performing the injection, the user can push the proximal end 32 of the piston rod 30 in a distal direction. In this case, the force applied to the piston rod 30 is a combination of the spring force and the force exerted by the user. The movement of the piston rod 30 can thus be accelerated, and the injection rate is thus increased. If the user stops pushing the piston rod 30, said piston rod becomes again driven by the spring 31 only.

According to the first, second, and third embodiment of the device, once the locking member 50, 60, 70 is in the released position, the piston rod 30 moves in a distal direction and keeps moving until the end of the injection.

According to the fourth embodiment of the device, the injection keeps going as long as the user pushed the button 71. If the user releases the button, the injection stops. As such, the user can selectively start and stop the injection by respectively pushing or releasing the button.

The injection device assembly is advantageously provided with a spacer 80 positioned in the container 40 in contact with the stopper 44, prior to the mounting of the container 40 on the device 1. The spacer 80 preferably includes a protrusion 81 on its distal end which is inserted into a corresponding recess 45 on the proximal end of the stopper 44, so that the stopper 44 and the spacer 80 are fixed together and glide together in the container 40 when pushed by the piston rod 30.

The spacer 80 absorbs a part of the mechanical effort transmitted by the piston rod 30 to the stopper 44 when the piston rod indirectly contacts the stopper. Hence, when pushed by the piston rod 30 via the spacer 80, the stopper 44 moves continuously and smoothly. To this end the spacer 80 is advantageously made of a rigid material, such as plastic or metal for example, and its length is adapted relatively to the volume of the composition contained in the medical container so as to reduce the space between the proximal end of the medical container and the surface of the composition: the smaller the volume of the composition, the longer the spacer.

The proximal end of the spacer 80 is adapted to contact the distal end of the piston rod 30, the contact surface between the spacer 80 and the piston rod 30 being preferably a flat surface so that the mechanical efforts are distributed on the entirety of said flat surface, thus improving the movement of the spacer 80 along with the stopper 44.

The invention claimed is:

1. An assisted injection device for injecting a composition contained in a medical container, comprising:
   a body adapted to receive a medical container in a fixed position relative to the body, the body being configured to be held in a user's hand,
   a spring-loaded piston rod comprising a spring, the piston rod being translationally movable inside the body between a proximal rest position allowing inserting of the medical container in the body and a distal operative position wherein the piston rod engages a stopper of the medical container and pushes the stopper in the medical container, and
   a blocking system comprising a locking member mounted on the body and configured to engage the piston rod, the locking member being movable between a locked position wherein the locking member cooperates with the body to retain the piston rod in the proximal rest position, and a released position wherein the locking member cooperates with the body to allow the piston rod to move from the proximal rest position to the distal operative position under a distally directed biasing force of the spring,
   wherein the piston rod includes a proximal end extending out of the body and configured to be pushed by the user in a distal direction to accelerate the movement of the piston rod to the distal operative position when the locking member is in the released position.

2. The assisted injection device according to claim 1, wherein the piston rod is provided with a transversal hole, and wherein the locking member is an insert which, when in the locked position, is inserted radially in the transversal hole of the piston rod, and when in the released position, is removed from the transversal hole.

3. The assisted injection device according to claim 2, wherein the insert is slidable on the proximal wall of the body opposite the medical container.

4. The assisted injection device according to claim 3, wherein the proximal wall of the body comprises a notch adapted to receive the insert slidable therein, the notch extending radially to the piston rod and being aligned with the hole of the piston rod when the piston rod is in the proximal rest position.

5. The assisted injection device according to claim 2, wherein the peripheral wall of the body of the device is provided with a transversal opening that forms a transversal passage through said body, and wherein when in the locked position, the insert is inserted radially in the transversal opening of the body and crosses the hole of the piston rod aligned therewith, and when in the released position, the insert is removed from the transversal opening.

6. The assisted injection device according to claim 1, wherein the peripheral wall of the body of the device is provided with a transversal opening that forms a transversal passage through said body, and wherein when in the locked position, the insert is inserted radially in the transversal opening of the body distally from the piston rod, so that the piston rod abuts the insert, and when in the released position, the insert is removed from the transversal through hole.

7. The assisted injection device according to claim 1, wherein the piston rod is provided with a narrowed section, and wherein the locking member is a latch provided with at least a first hole and a second hole in communication with each other, the diameter of the first hole being smaller than the diameter of the piston rod and the diameter of the second hole being greater than the diameter of the piston rod, the latch being radially slidable between the locked position wherein the first hole is aligned with the piston rod and accommodates the narrowed section of the piston rod, and the released position wherein the second hole is aligned with the piston rod and crossed by said piston rod.

8. The assisted injection device according to claim 7, wherein the latch is slidable on the proximal wall of the body opposite the medical container.

9. The assisted injection device according to claim 1, wherein the piston rod is provided with a toothed rack, and wherein the blocking system comprises a button mounted on the body of the device and coupled to the locking member which is a wing, the wing being pivotably mounted on a structure fixed to the body, the wing being pivotably movable between the locked position wherein the button is released and the wing engages the toothed rack so as to block the piston rod, and the released position wherein the button is pushed and the wing disengages the toothed rack so as to allow the piston rod to move.

10. The assisted injection device according to claim 9, wherein the button is a spring-loaded button.

11. The assisted injection device according to claim 1, wherein the body comprises a container holder system configured to receive at least a portion of the medical container and to hold the medical container aligned with the movement direction of the piston rod so that when moving from the proximal rest position to the distal operative position, the piston rod engages the stopper of the medical container and pushes the stopper in the medical container to inject the composition.

12. The assisted injection device according to claim 11, wherein the container holder system comprises:
- a slot provided in the peripheral wall of the body that leads to a housing configured to receive at least a portion of the medical container and to maintain the medical container in a fixed position aligned with the movement direction of the piston rod, and
- a through groove provided in the distal wall of the body, continuous with the slot and extending in the distal wall from the slot, the groove being configured to guide the medical container inserted via the slot to the housing.

13. An assisted injection device assembly comprising the assisted injection device according to claim 1 and a medical container mounted thereon.

14. The assisted injection device assembly according to claim 13, wherein said assembly further comprises a spacer configured to be fixed to the stopper, the spacer being configured to be contacted and pushed by the piston rod along with the stopper when the piston rod is moving from the proximal rest position to the distal operative position.

* * * * *

UNITED STATES PATENT AND TRADEMARK OFFICE
CERTIFICATE OF CORRECTION

PATENT NO. : 11,612,694 B2
APPLICATION NO. : 16/632523
DATED : March 28, 2023
INVENTOR(S) : Julien Gagliano It is certified that error appears in the above-identified patent and that said Letters Patent is hereby corrected as shown below:

In the Claims

Column 10, Line 66, Claim 3, delete "the" and insert -- a --

Column 11, Line 5, Claim 4, after "the" insert -- transversal --

Column 11, Line 8, Claim 5, delete "the" and insert -- a --

Column 11, Line 12, Claim 5, before "hole" insert -- transversal --

Column 11, Line 16, Claim 6, delete "the" and insert -- a --

Column 11, Line 19, Claim 6, delete "the" and insert -- an --

Column 11, Line 22, Claim 6, delete "through hole." and insert -- opening. --

Column 11, Line 36, Claim 8, delete "the" and insert -- a --

Column 12, Line 22, Claim 12, delete "the" and insert -- a --

Column 12, Line 27, Claim 12, delete "the" and insert -- a --

Column 12, Line 29, Claim 12, after "the" insert -- through --

Signed and Sealed this
Sixteenth Day of May, 2023

Katherine Kelly Vidal
*Director of the United States Patent and Trademark Office*